United States Patent [19]
Kung

[11] Patent Number: 4,476,049
[45] Date of Patent: Oct. 9, 1984

[54] METHOD FOR THE EXTRACTION OF IMMUNE INTERFERON

[75] Inventor: Hsiang-Fu Kung, Verona, N.J.

[73] Assignee: Hoffmann-La Roche Inc., Nutley, N.J.

[21] Appl. No.: 534,039

[22] Filed: Sep. 20, 1983

[51] Int. Cl.³ .................... A61K 45/02; C07G 7/00
[52] U.S. Cl. .................... 260/112 R; 424/85; 435/240; 435/811; 435/948
[58] Field of Search .............. 424/85; 260/112 R; 435/811, 948, 240

[56] References Cited

U.S. PATENT DOCUMENTS

| | | | |
|---|---|---|---|
| 3,981,991 | 9/1976 | Stewart et al. ................ | 424/85 |
| 4,017,600 | 4/1977 | Stewart et al. ................ | 424/85 |
| 4,357,422 | 11/1982 | Giard et al. ................ | 435/948 X |
| 4,382,027 | 5/1983 | Braude ................ | 260/112 R |
| 4,388,234 | 6/1983 | Horecker ................ | 260/112.5 R |
| 4,414,150 | 11/1983 | Goeddel ................ | 260/112 R X |

OTHER PUBLICATIONS

Method in Enzymology, vol. 22, p. 212, (1971).

*Primary Examiner*—Howard E. Schain
*Attorney, Agent, or Firm*—Jon S. Saxe; George M. Gould; Steve T. Zelson

[57] ABSTRACT

A method for the extraction of intact recombinant human immune interferon with guanidine-HCl is disclosed. This method permits the purification to homogenity of intact recombinant human immune interferon.

7 Claims, 3 Drawing Figures

FIG. 2

Sequence Comparison Between DNA Predicted Sequence and the 15K and 18K rIFN-γ

```
     1
    Cys - Tyr - Cys - Gln - Asp - Pro - Tyr - Val - Lys - Glu - Ala - Glu - Asn - Leu - Lys¹⁵
15K  →*    →     →                →     →     →     →     →     →     →     →     →     →
18K  →*    →     →                →     →     →     →     →     →     →     →     →     →

30
    Lys - Tyr - Phe - Asn - Ala - Gly - His - Ser - Asp - Val - Ala - Asp - Asn - Gly - Thr
15K  →     →     →     →           →     →     →     →     →     →     →     →     →     →
18K  →     →     →     →           →     →     →     →     →     →     →     →     →     →

35                                                                  120
    Leu - Phe - Leu - Gly - Ile ================================================== Met
15K  →     →     →     →

121                                                                      131                      135
    Ala - Glu - Leu - Ser - Pro - Ala - Ala - Lys - Thr - Gly - Lys ================================
15K  →     →     →     →     →     →     →     →     →     →    →||

146
      - Met - Leu - Phe - Arg - Gly - Arg - Arg - Ala - Ser - Gln →||
18K     →     →     →     →     →     →     →     →     →     →
```

Figure 2 — Footnotes

The arrow (→) indicates the residue identified by sequence determination.
The star (*) indicates the cysteine residue identified in the form of C14 carboxymethylated cysteine.
Vertical bars (||) indicates the C-terminal end of the recombinant protein.

FIG. 3
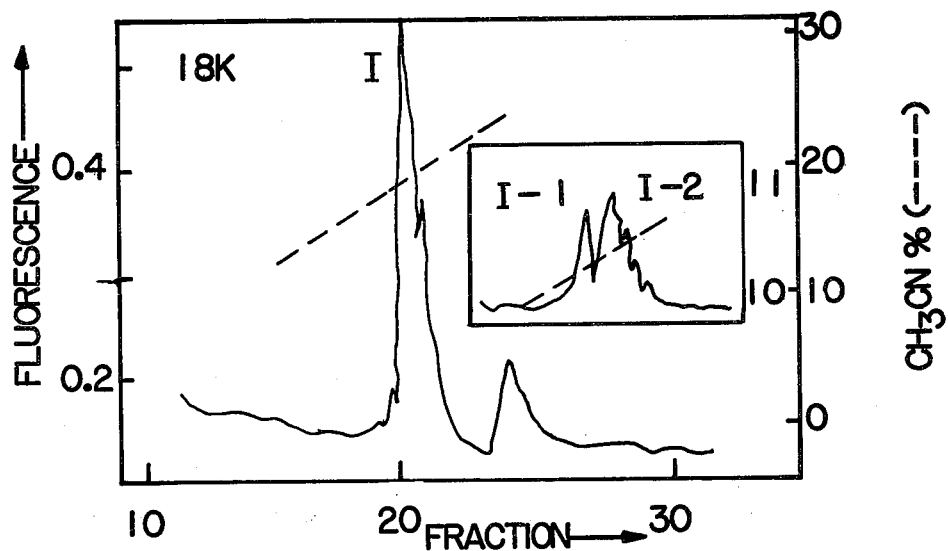
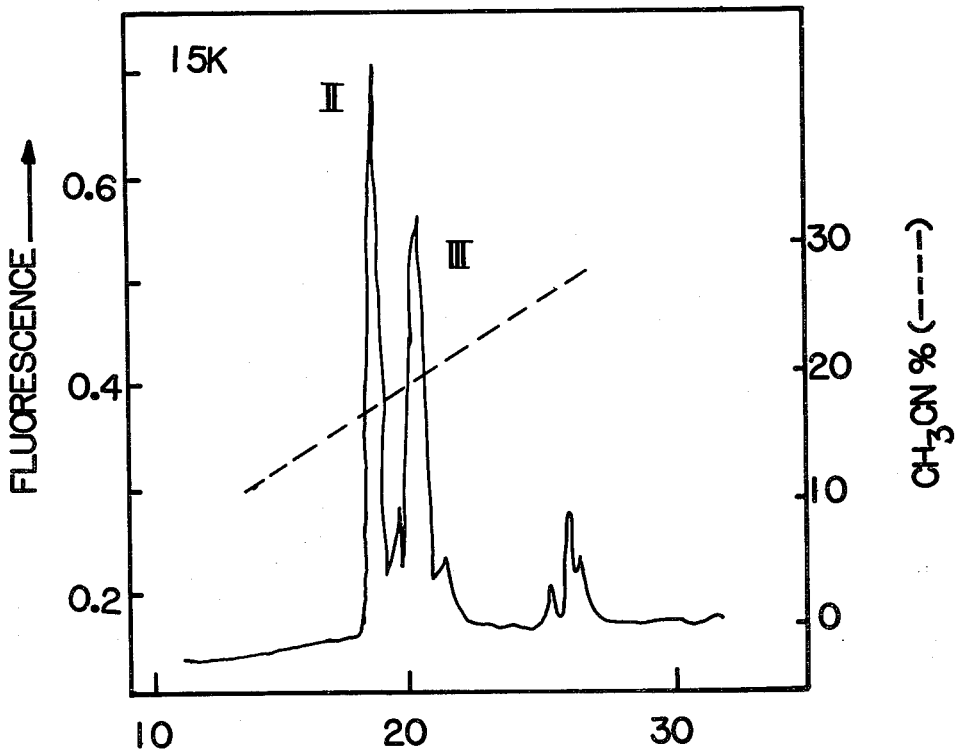

METHOD FOR THE EXTRACTION OF IMMUNE INTERFERON

FIELD OF THE INVENTION

This invention relates to a method for extraction of immune interferon from a microorganism preparation which contains this protein.

BRIEF DESCRIPTION OF THE FIGURES

FIG. 2 illustrates the comparison between the predicted DNA sequence of recombinant human immune interferon and the actual DNA sequence of the 15K and 18K rIFN-$\gamma$ species.

FIG. 3 illustrates the separation of C-terminal CNBr peptides of the 15K and 18K rIFN-$\gamma$.

BACKGROUND OF THE INVENTION

Figure 1:
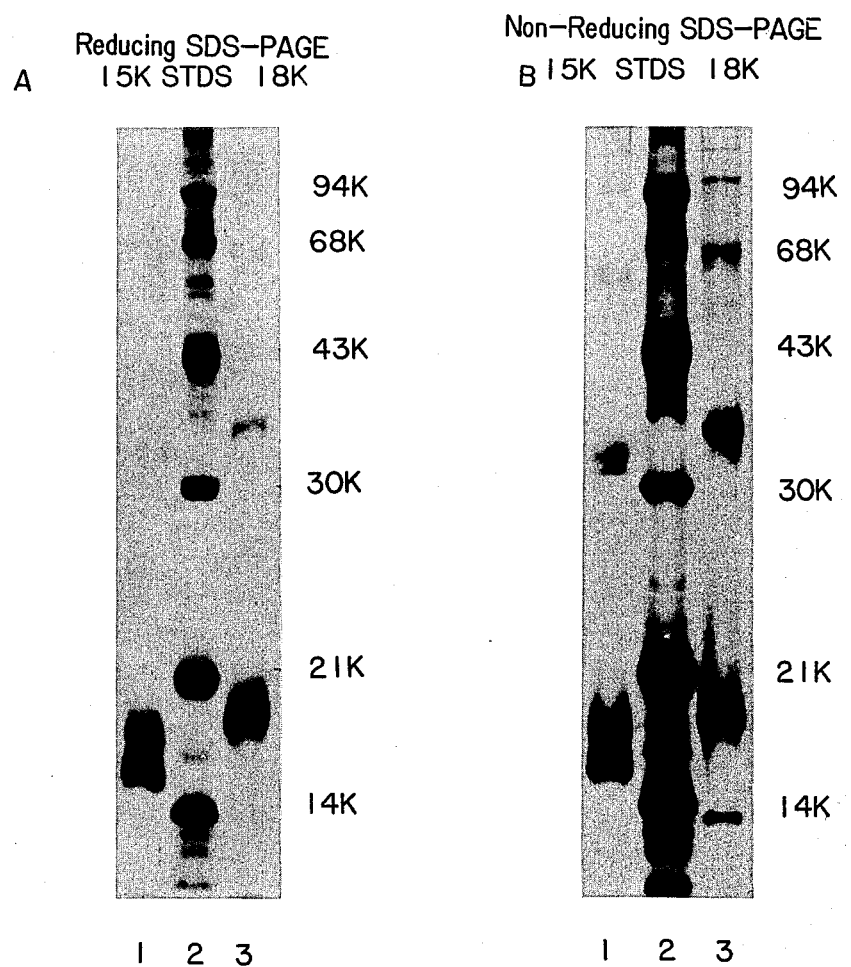
FIG. 1 illustrates sodium dodecyl sulfate-polyacrylamide gel electrophoresis of purified recombinant human immune interferon in photo "A" reducing condition (0.7M-$\beta$ mercaptoethanol in the sample loading buffer) and in "B" non-reducing condition.

The prior art has devised various methods for effecting the extraction and purification of the family of antiviral proteins known as interferon. To date there are three known major classes of interferon: INF-$\alpha$ (leukocyte), INF-$\beta$ (fibroblast) and INF-$\gamma$ (immune). Although the various interferon classes may be related in terms of antiviral, anti-proliferative or structural arrangement, the prior art has had so far been unable to devise a uniform method for the extraction and purification of all of these classes. Indeed, many of the processes useful for the extraction and purification of leukocyte interferon from a crude mixture of other proteins and cell debris would not work to extract and purify out fibroblast or immune interferon from the same kind of preparation.

The extraction step in the purification processes of the prior art typically involved either the mechanical (i.e. sonification) or chemical lysis of microorganisms which have produced, often through recombinant techniques, the desired foreign protein. However, during this mechanical or chemical lysis procedure various cellular proteases are also released into the mixture. These proteases are then free to enzymatically act upon and degrade the foreign protein in the mixture. These proteases can, therefore, hinder or inhibit the purification to homogeniety of the complete or mature and biologically active form of the foreign protein.

It is, therefore, an object of the present invention to provide a method which overcomes the limitations of the prior art extraction techniques whereby the intact sequence form of immune interferon is present and whereby proteolytic fragments are eliminated from the purified immune interferon preparation.

Summary of the Invention

Broadly stated, this invention comprises a method for extracting an intact sequence form of recombinant human immune interferon from a preparation containing this protein. More specifically, this invention comprises extracting immune interferon from microorganisms wherein the extraction is performed with a reagent, such as guanidine-HCl, which inhibits protease or enzyme activity and which does not effect the activity of the desired protein. The remaining purification procedure steps after guanidine-HCl extraction may be by suitable means those known to those skilled in the protein purification art.

Description of the Preferred Embodiments

It has been discovered in the case of immune interferon, that extraction with any of the conventional techniques such as sonification or mechanical lysis described in the prior art will not yield immune interferon with an intact or complete amino acid sequence. Only recently has recombinant technology advanced to the point at which it is possible to obtain sufficient quantities of rINF-$\gamma$ so as to characterize it and determine its amino acid sequence. When conventional prior art techniques were utilized to extract rINF-$\gamma$ preparations and the amino acid sequence of purified material was determined, it was discovered that the purified preparation was, in fact, comprised of a variety of related protein species of different molecular weight. It has further been discovered by amino acid sequencing that these proteins species are actually the intact sequence form of immune interferon in combination with proteolytic fragments of the intact sequence protein. Therefore, the prior art has yet been unable to extract and purify to homogenity the intact form of immune interferon free of other proteolytic fragment of immune interferon.

It has been discovered that the degradation of rIFN-$\gamma$ can be prevented with the use of a reagent, such as, guanidine-HCl, which inhibits protease of enzyme activity and which does not effect the activity of the rIFN-$\gamma$, in the initial extraction step of a purification procedure so as to obtain homogeneous and intact molecules. Sonification of frozen cells in the absence of guanidine-HCl yielded mainly the proteolytic product (15K rIFN-$\gamma$, i.e., removal of C-terminal amino acid residues No. 132–146). Amino acid composition and N-terminal sequence of the intact molecule was consistent with that expected from the DNA sequence. The DNA base sequence of rIFN-$\gamma$ as used throughout this specification is as described in reference 1.

Generally stated, this invention comprises a method for extracting recombinant human immune interferon with a complete and intact sequence from a preparation of microorganisms containing this protein by treating a preparation of transformed microorganisms which produce recombinant human immune interferon with a reagent (or mixture of reagents), such as guanidine-HCl, which inhibit protease or enzyme activity and which does not effect the activity of the desired protein. Additionally, it has surprisingly been found that immune interferon retains its biological activity after a guanidine-HCl extraction step even though guanidine-HCl destroys the biological activity when added to a purified preparation of immune interferon. It is preferred that in the practice of this invention that the transformed microorganisms be suspended in the guanidine-HCl.

The anti-proteolytic agent of this invention may be any guanidinium salt. Among such guanidinium salts there are included the organic acids such as for example acetic acid and the mineral acids such as for example the hydrohalides, i.e., hydrobromide, hydrochloride, hydrofluoride and hydroiodide, or thiocyanate. The preferred guanidinium salt is guanidine hydrochloride. The concentration of guanidinium salt in the treatment of the microorganisms is not critical in that any effective amount may be used. It is preferred, however, that a 3 to 6M solution of the guandinium salt be used for treating the microorganisms and that about 3 to 9 volumes of the salt solution per gram of microoorganisms be used. The concentration of the salt may be achieved by making the salt up in a solvent such as water or aqueous buffers, such as ammonium acetate, pyridine acetic acid, and the like. It is also foreseeable that in the practice of this invention other protease inhibitor reagents may be used, such as urea.

Purified rIFN-γ can be obtained by applying *E. coli* supernatant after extraction and appropriate dilution directly on purification means using a novel monoclonal antibody purification step. The extraction and purification process can also be automated for large-scale production. The eventual availability of large amounts of homogenous rIFN-γ will permit extensive clinical trials, biological studies, X-ray crystallography and structure-function studies.

Further preferred embodiments will be illustrated in the following specification and examples.

Recombinant human immune interferon (rIFN-γ) produced in *E. coli* is preferrably extracted from frozen cell paste by 7M guanidine-HCl and purified by suitable purification means such as through novel monoclonal antibody affinity columns. A purified interferon with apparent M.W.≃18,000 daltons on sodium dodecyl sulfate-polyacrylaminde gel electrophoresis has been obtained by guanidine extraction whereas a lower M.W. species (major species≃15,000 daltons) was isolated by sonification in the absence of guanidine. The amino terminal sequence of both the 18K and 15K proteins were consistent with the sequence predicted from the DNA coding for this human immune interferon protein.

In a preferred embodiment of this invention, the microorganisms employed as the recipient in the fermentation procedures and unless otherwise noted, is the microorganism *Escherichia coli* K-12 strain 294 as described in British Patent Publication No. 2055382A and which is incorporated by reference herein. This microorganism has been deposited with the American Type Culture Collection, ATCC Accession No. 31446, deposited Oct. 28, 1978. Furthermore, all recombinant DNA work herein was performed in compliance with applicable guidelines of the National Institutes of Health.

The invention, in its most preferred embodiments, is described with reference to *E. coli*, including not only *E. coli* K-12 strain 294, defined above, but also other known *E. coli* strains such as *E. coli* MA210 or RR1 (ATCC #31343), or other microbial strains many of which are publicly available or are deposited and available from recognized microorganism depository institutions, such as the American Type Culture Collection (ATCC)-cf. the ATCC catalog listing.

The C-terminal sequence was determined by analyzing and sequencing purified C-terminal peptide after CNBr treatment. The amino acid composition and sequence of the C-terminal peptide released from the 18K rIFN-γ matched with the predicted sequence of rIFN-γ indicating that the 18K species is the intact molecule. On the other hand, a different CNBr cleaved peptide was released from the C-terminus of the 15K rIFN-γ. Based on amino acid and sequence analysis, the different peptide corresponded to the amino acid residues No. 121-131 indicating that the 15K species was a proteolytic product.

This invention will be further illustrated by the following examples.

Monoclonal antibodies were made against a synthetic polypeptide containing the last 16 amino acid residues of the C-terminal peptide of rIFN-γ. One of the monoclonal antibodies (Moγ2-11.1) was used for the purification of rIFN-γ. More specifically, the monoclonal antibodies and antibody affinity column of this invention were prepared as described in co-pending patent application No. PCT/JP83/00174, filed 5/31/83 in Japan and as detailed below in the following examples.

EXAMPLE 1

Synthesis of carrier protein-polypeptide complex used as antigen

The polypeptide H-Lys-Arg-Lys-Arg-Ser-Gln-Met-Leu-Phe-Arg-Gly-Arg-Arg-Ala-Ser-Gln-OH was coupled with thyroglobulin (hereinafter, TG) according to the method of Goodfriend et al. (Science, 144, 1334, 1964). The above-mentioned peptide can be produced by the conventional methods of peptide synthesis. Either of the solid phase method and liquid phase method may be used, although the liquid phase synthetic method is advantageous in many cases. Such methods of peptide synthesis are described, for example, by Schroder and Lubke in "The peptides",. vol. 1, Academic Press, New York, U.S.A., 1966, or by Izumiya et al. in "Peptide Syntheses", Maruzen, Tokyo, Japan, 1975, or by Haruaki Yajima in "Experiments in Biochemisty, vol. 1, pages 207-400", Tokyo Kagaku Dojin, 1977, and include, among others, the azide method, chloride method, acid anhydride method, mixed acid anhydride method, DCC method, active ester method, method using Woodward reagent K, carbodiimidazole method, oxidation reduction method and DCC/additive (e.g. HONB, HOBt, HOSu) method.

Said peptide can be produced by condensing a reactive carboxyl-containing starting material corresponding to one of the two fragments resulting from division of said peptide at any site of the peptide bonding thereof with a reactive amino-containing starting material corresponding to the other fragment by any of the conventional peptide synthesis methods and, in case the condensation product has a protective group, eliminating the protective group in the conventional manner.

The method of protecting a functional group which should not be involved in the reaction between the materials, the protective group to be used in such protection, the method of eliminating such protective group and the method of activating the functional group to be involved in the reaction, for instance, can be selected adequately from among known ones or means.

Thus, 2.5 mg of said polypeptide was mixed with 3.75 mg of TG and, following addition of 2 ml of 50 mM phosphate buffer, the mixture was stirred well in ice water. Thereto was gradually added drop by drop a solution of 30.4 mg of carbodiimide hydrochloride in 200 ml of distilled water. Thereafter, the mixture was stirred in ice water for 3 hours. After the reaction, dialysis was performed against distilled water to a sufficient extent, followed by lyophilization to give 4.7 mg of a protein complex.

EXAMPLE 2

Preparation of antigen for Enzyme Immunoassay (EIA) for antibody detection

The antigen for EIA was prepared according to Kitagawa et al. (Journal of Biochemistry, vol. 79, page 233, 1976).

(i) Introduction of a maleimido group into the polypeptide

The polypeptide (350 nmoles) as obtained in Example 1 (xvi) was dissolved in 1 ml of 100 mM phosphate buffer (pH 6.8), and the solution was added to a solution of 585 ug (1.75 umoles) of N-(4-carboxycyclohexylmethyl)maleimide. N-hydroxy-succinimide ester in 70 μl of N,N-dimethylformamide. The mixture was stirred at 30° C. for 30 minutes. After the reaction, fractionation was performed using a Sephadex G-25 column to give 185 nmoles of a polypeptide fraction with the maleimido group introduced therein.

(ii) Coupling of the maleimido-group-containing polypeptide with Beta-D-galactosidase The maleimido-containing polypeptide (16.5 nmoles) as obtained in Example 3 (i) was mixed with 3.3 nmoles of Beta-D-galactosidase. After 18 hours of reaction at 4° C., 412,5 nmoles of Beta-mercaptoethanol was added for terminating the reaction. The Beta-D-galactosidase-coupled polypeptide was fractionated on a Sepharose 6B column and used for the subsequent experiments.

EXAMPLE 3

Immunization

Each of 6 female BALB/C mice aged 7 to 8 weeks was subcutaneously inoculated with 40 ug (on the protein basis) of the protein complex obtained in Example 1 (as the antigen) in intimate admixture with Freund's complete adjuvant (primary immunization). Two weeks after the primary immunization, the mice were subcutaneously inoculated with the antigen at the same dose as above in intimate admixture with Freund's incomplete adjuvant (secondary immunization). Further two weeks later, a third immunization was made in the same manner as in the secondary immunization. Six days after the third immunization, partial blood sampling was made from the mice and the serum antibody titers were determined by the EIA method described in Example 4. The mouse numbered γ-2 gave the highest antibody titer and was subjected to the final immunization by intravenous inoculation with 120 ug of the antigen dissolved in 0.5 ml of aqueous sodium chloride. The antibody titer data for each mouse are shown in Table 1.

TABLE 1

Antipeptide antibody titers in immunized mice

| Mouse No. | B/T (%) Primary immunization[1] | Secondary immunization[2] | Third immunization[3] |
|---|---|---|---|
| γ-1 | —[4] | N.D | 24.5 |
| 2 | N.D[5] | 19.3 | 35.3 |
| 3 | — | N.D | 24.7 |
| 4 | N.D | 1.3 | 1.7 |
| 5 | N.D | 1.8 | 5.0 |
| 6 | — | N.D | 0.8 |
| Normal mouse | 0.6 | 0.1 | N.D |

[1] Serum dilution ratio: 1/1000
[2] Serum dilution ratio: 1/6300
[3] Serum dilution ratio: 1/7800
[4] —: Not detectable
[5] ND: Not determined
B/T: (Bound enzyme activity/total added anzyme activity) × 100

EXAMPLE 4

Cell fusion

Immunization was performed by the method described in Example 5. Three days after the final immunization, the spleen was excised from the γ-2 mouse, filtered under pressure through a stainless mesh, and suspended in Eagle's minimum essential medium (MEM) to give a spleen cell suspension. For cell fusion, BALB/C mouse-derived P3-x63.Ag8.U1 (P3U1) myeloma cells were used (Current Topics in Microbiology and Immunology, vol. 81, page 1, 1978). Cell fushion was performed by the original method (Nature, vol. 256, page 495, 1975). Thus, spleen cells and P3U1 cells were separately washed three times with serum-free MEM and mixed at a ration of 5:1 (in number of cells). The mixture was centrifuged at 800 rpm for 15 minutes, whereby the cells were settled. After thorough removal of the supernatant, the sediment was lightly loosened, 0.3 ml of 45% polyethylene glycol (PEG) 6000 (Koch-Light) was added, and the mixture was allowed to stand in a warm water tank maintained at 37° C. for 7 minutes so as to effect cell fusion. Thereafter, MEM was added thereto at a rate of 2 ml per minute. After addition of 12 ml in total of MEM, the resulting mixture was centrifuged at 600 rpm for 15 minutes, followed by removal of the supernatant. The cell sediment was suspended in RPMI-1640 medium supplemented with 10% fetal calf serum (RPMI1640-10FCS) in a concentration of $2 \times 10^5$ P3U1 cells/ml and each of 144 wells on 24-well multidishes (Linbro) was seeded with 1 ml of the suspension. After seeding, the cells were incubated at 37° C. in a 5% carbon dioxide gas incubator. After 24 hours, HAT-selective culture was started by adding RPMI1640-10FCS medium supplemented with HAT ($1 \times 10^{-4}$M hypoxanthine, $4 \times 10^{-7}$M aminopterin, $1.6 \times 10^{-5}$M thymidine) (HAT medium) in an amount of 1 ml per well. The HAT-selective culture was continued while 1 ml of the old medium was replaced by 1 ml of HAT medium 3,5 and 7 days after start of the culture. The growth of hybridomas was noted 10 to 14 days after cell fusion. When the culture broth turned yellow (about $1 \times 10^6$ cells/ml), the supernatant was collected and examined for the presence of antibody by the EIA method. In this manner, supernatants from 141 wells in which hybridoma growth had been noted were examined. Two wells (γ2-11 and γ2-100) afforded intense antibody activity and other two wells (γ2-62 and γ2-70) presented weak antibody activity.

EXAMPLE 5

Cloning

Hybridomas from 3 wells (γ2-11, 62 and 100) which were positive in antibody activity were cloned by the limiting dilution method. Thus, hybridoma cells were suspended in RPMI1640-20FCS in a concentration of at least about 2 hybridoma cells/ml and the suspension was distributed in 0.1-ml portions into the wells on a 96-well microplate (Nunc). In said distribution, $5 \times 10^5$ per well of BALB/C mouse thymocytes were added as feeder cells. As a result, cell proliferation was observed in about 2 weeks. The supernatant was then collected and examined for the presence of antibodies by the EIA method as described in Example 4. Antibody activity was noted in 8 out of 19 clones from γ2-11 well, in 3 out of 54 clones from γ2-62 well, and in 5 out of 47 clones from γ2-100 well (Table 2).

TABLE 2

Anti-peptide antibody activity of cloned hybridomas

| Hybridoma No. | B/T (%) |
|---|---|
| γ2-11 | |
| 1 | 68 |
| 2 | 31 |

TABLE 2-continued

Anti-peptide antibody activity of cloned hybridomas

| Hybridoma No. | B/T (%) |
|---|---|
| 3 | 63 |
| 6 | 68 |
| 7 | 67 |
| 9 | 69 |
| 12 | 42 |
| 18 | 60 |
| τ2-62 | |
| 14 | 20 |
| 16 | 21 |
| 34 | 16 |
| τ2-100 | |
| 2 | 69 |
| 3 | 70 |
| 16 | 56 |
| 25 | 80 |
| 46 | 33 |
| Hyperimmune mouse serum | 35 |

EXAMPLE 6

Binding capacity of monoclonal antibody to IFN-γ

The binding capacity of monoclonal antibody to IFN-γ was determined by the following method. To 300 ul of a 3% solution of cellulose coupled with rabbit anti-mouse IgG antibody, 300 ul of the culture supernatant for each of 2 or 3 cloned cell lines from each of γ 2-11, γ 2-62 and γ 2-100 wells was added, and the reaction was allowed to proceed at room temperature for 12 to 20 hours. Thereafter, the cellulose was thoroughly washed with physiological saline, and 550 U/ml of IFN-γ obtained by the procedure mentioned below was added thereto. After 3 to 4 hours of reaction, the supernatant was collected and the IFN-γ obtained by the procedure mentioned below was added thereto. After 3 to 4 hours of reaction, the supernatant was collected and the IFN-γ activity therein was determined by the cytopathic effect (CPE) reading method using a microplate (Applied Microbiology, vol. 16, page 1706, 1968). Thus, 50 ul of MEM was placed in each well of a 96-well microplate (Nunc) and 50 ul of a WISH cell suspension ($4 \times 10^5$ cells/ml) in 20% FCS-containing MEM was added, and incubation was conducted in a carbon dioxide gas incubator at 37° C. About 35 hours later, when cells in the IFN sample-free well showed 100% CPE, each well was microscopically observed for the estimation of CPE, and the reciprocal of the dilution factor for the IFN sample in that well in which 50% CPE was noted was referred to as the IFN titer.

The IFN-γ sample used was the supernatant collected 72 hours affer stimulation of human peripheral lymphocytes with 40 ug/ml of concanavalin A and 15 ng/ml of 12-0-tetra-decanoylphorbol-13-acetate. Each ml of this culture supernatant contained 4400 units of human IFN-γ (acid-labile and unstable to pH treatment). If antibodies having binding capacity to IFN-γ are present in the cloned cell culture supernatant, then the added IFN-γ should be conjugated to the antibodies on cellulose and reduction in IFN-γ activity of the supernatant should occur. As a result, for the clone γ 2-11, relatively intense binding activity to IFN-γ was noted and 50-75% of the added IFN-65 (550 U/ml) was conjugated to antibodies (Table 3).

TABLE 3

Absorption of IFN-γ activity by monoclonal antibodies

| Hybridoma culture supernatant | Remaining IFN activity (U/ml) | |
|---|---|---|
| | Experiment 1 | Experiment 2 |
| τ2-11.1 | 138 | 275 |
| τ2-11.2 | 207 | N.D. |
| τ2-11.6 | N.D. | 275 |
| τ2-62.2 | 275 | 550 |
| τ2-62.3 | 275 | 550 |
| τ2-100.2 | 550 | N.D. |
| τ2-100.3 | 550 | N.D. |
| — | 550 | 550 |

EXAMPLE 7

Ascites formation by monoclonal antibody-producing hybridomas

Ascites formation was caused by intraperitoneal inoculation of BALB/c mice intraperitoneally pretreated with 0.5 ml of mineral oil with $1 \times 10^6$, γ 2-11.1 clone cells capable of producing antibodies having IFN-γ-binding activity. Ten days after intraperitoneal administration of hybridomas, the ascitic fluid was taken and examined for antibody activity, which was detected until $10^7$-fold dilution. While the antibody activity of the corresponding clone cell culture supernatant was detected until $10^4$-fold dilution, the formation of ascites (ascitization) led to an about 1000 times increase in antibody activity.

EXAMPLE 8

Monoclonal antibody purification

Using 4 ml of the ascitic fluid obtained in Example 9 as the starting material, monoclonal antibody purification was performed by the method of Staehelin et al. (Journal of Biological Chemistry, vol. 256, page 9750, 1981). Thus, the ascitic fluid was first centrifuged at 10,000 rpm for 15 minutes to remove fibrin-like substances therefrom and then diluted with phosphate buffer-saline (PBS: 8.1 mM $NaH_2PO_4$, 1.5 mM $KH_2PO_4$, 2.7 mM KCl, 137 mM NaCl; pH 7.2) to a concentration at which the ultraviolet absorption at 280 nm ($A_{280}$) for said dilution would range from 12 to 14. Thereafter, saturated aqueous ammonium sulfate was added to the sample dilution to a concentration of 47% for the sulfate. The mixture was stirred at 4° C. for 60 minutes to effect salting out and then centrifuged (10,000 rpm, 15 minutes) to give a precipitate. The precipitate was dissolved in 20 mM Tris buffer (pH 7.9) containing 50 mM NaCl and dialyzed against 2 liters of the same buffer. Two hours later, the dialyzing solution was replaced by a fresh 2-liter portion of the same solution and the dialysis was continued for further 15 hours. Thereafter, the precipitate was removed by centrifugation at 10,000 rpm for 15 minutes, and the supernatant was adjusted to a concentration such that the $A_{280}$ value became 20-30. This sample was subjected to fractionation on a DEAE-cellulose column (8 ml, Whatman $DE_{52}$) equilibrated with a sufficient amount of Tris buffer containing 50 mM NaCl, elution being made with Tris buffer containing 50 mM NaCl at a flow rate of 1.5 ml/minutes. Under these conditions, the antibody activity was detected mainly in effluent fractions (FIG. 1). Antibody confirmation was made by SDS-poly-acrylamide gel electrophoresos (SDS-PAGE) method as described by Laemmli et al. (Nature, vol. 227, page 680, 1970). Thus, some of the fractions obtained by ammonium sulfate salting out and DEAE-cellulose fractionation were each subjected to reduction with 2-mercaptoethanol, followed by 17% SDS gel electrophoresis at 30 volts for 24 hours. In agreement with the antibody activity peaks, two bands were noted at positions corresponding to molecular weights of about 55 kilodaltons (H chain) and about 28 kilodaltons (L chain) (FIG. 2). The thus-purified antibody fraction 17 was examined for IFN-γ-binding activity by adding IFN-γ (2200 U/ml). It was thus found that about 50% of IFN-γ was bound to the antibody (Table 4).

TABLE 4

| Sample | Dilution | Residual IFN activity (U/ml) |
| --- | --- | --- |
| γ2-11.1 fraction 17 | $10^{-1}$ | 1100 |
|  | $10^{-2}$ | 1100 |
|  | $10^{-3}$ | 2200 |
|  | $10^{-4}$ | 2200 |
| Anti-IgE monoclonal antibody | $10^{-1}$ | 2200 |
|  | $10^{-2}$ | 2200 |
|  | $10^{-3}$ | 2200 |
|  | $10^{-4}$ | 2200 |

EXAMPLE 9

Subclass to which monoclonal antibodies belong

The fraction 17 purified by the method of Example 8 was diluted 10 times and subjected to agar precipitation reaction (Ouchterlony test: Immunological Methods, Gel-Diffusion Technique, Blackwell, Oxford, 1964) using goat anti-mouse IgG1, G2a, G2b and G3 antibodies (Miles) so the IgG subclass to which γ 2-11.1 monoclonal antibodies might belong could be identified. A single distinct band was found between the monoclonal antibody and the goat anti-mouse IgG2b antibody, while no band formation was noted between the monoclonal antibody and other anti-antibodies. Accordingly, said monoclonal antibody was found to belong to IgG2b (Table 5).

TABLE 5

| | Monoclonal anitbody subclass | |
| --- | --- | --- |
| Antigen | Antibody | Precipitation curve |
| Monoclonal antibody of the present invention (fraction 17) | Anti-IgG1 | — |
| Monoclonal antibody of the present invention (fraction 17) | Anti-IgG2a | — |
| Monoclonal antibody of the present invention (fraction 17) | Anti-IgG2b | + |
| Monoclonal antibody of the present invention (fraction 17) | Anti-IgG3 | — |

EXAMPLE 10

Twenty-five ml (65.3 mg) of the monoclonal antibody from the effluent fractions as purified by the procedure of Example 8 was dialyzed overnight against 0.1M NaHCO$_3$ (pH 8.3). Separately, 25 ml of AFFI-GEL 10 (Bio-Rad) was thoroughly washed with water using a glass filter, suspended in 0.1M NaHCO$_3$ (pH 8.3) and mixed with the above antibody. The mixture was stirred gently at 4° C. for 4 hours to effect the reaction, and then allowed to stand at 4° C. overnight. The AFFI-GEL 10 was washed well with 0.1M NaHCO$_3$ (pH 8.3) using a glass filter. To the gel was added 25 ml of a solution (pH 8.0) containing 0.1M ethanolamine and 0.15M NaCl. The mixture was shaken at 4° C. for an hour so as to block possibly remaining unreacted active groups. Then, the gel was washed well with PBS, and suspended in 25 .ml of 0.1% NaN$_3$-containing PBS. The suspension was stored at 4° C. Based on the amount of the added antibody and the amount of the antibody in the recovered filtrate, it was found that the antibody was conjugated to the gel in a proportion of 2.35 mg/ml of gel. A column was packed with the reaction product obtained in this manner and used as an antibody column.

EXAMPLE 11

E. coli RR1 (pRK248cI$_{ts}$, pRC231/IFI-900) (the construction of this recombinant organism is detailed in the co-pending case U.S. Ser. No. 397,388, filed July 12, 1982, Crowl-inventor, and which is incorporated by reference herein) was used for rINF-γ fermentations. The pRK248cI$_{ts}$ and pRC231/IFI-900 plasmid contained temperature sensitive Lambda repressor and IFN-γ gene respectively. Expression of rIFN-γ gene was under the control of the P$_L$ promoter.

Overnight cultures of E. coli RR1 (pRK248cI$_{ts}$, pRC231/IFI-900) were grown in LB broth at 30° C. One liter of the overnight culture was diluted to 10 liters with minimal M-9 medium containing casamino acids. At logarithmic growth, the culture was shifted from 30° C. to 42° C. and continued to grow at 42° C. for 2–3 hours. Bacteria were harvested by centrifugation and the bacterial pellets were stored at −20° C. until used. All fermentations and procedures were performed in accordance with recombinant DNA guidelines of the National Institutes of Health.

Monoclonal antibodies were made against synthetic C-terminal peptide of rIFN-γ (last 16 amino acid residues) in the manner described above. One of the monoclonal antibody (Mo γ 2-11.1) was used for the purification of rIFN-γ. The coupling of monoclonal antibody (Mo γ 2-11.1) to Affi-Gel 10 (Bio-Rad) for the preparation of the immunoadsorbent column. The coupling methodology was described in an analogous fashion as described in reference (2).

Iodo [1-$^{14}$C] acetic acid was obtained from New England Nuclear, cyanogen bromide from Pierce Inc., carboxypeptidase A from Sigma Inc., fluorescamine from Hoffman-La Roche Inc., C-8 and C-18 reverse-phase chromatographic columns from Supelco Inc. All the solvents used for protein characterization were re-distilled over ninhydrin.

Carboxymethylation of rIFN-γ by $^{14}$C-iodoacetic acid was carried out in the presence of 6M guanidine HCl as described in published procedures of reference (3). Excess reagent was removed by HPLC on C8 reverse-phase column. Carboxypeptidase digestion was performed in 0.2M NH$_4$HCO$_3$ as described in reference (4).

The rIFN-γ was treated with CNBr (100-fold molar excess over methionine) in 70 percent formic acid as described in reference (5) CNBr peptides were separated by HPLC on C-18 reverse-phase column. A linear gradient of 0 to 70 percent of CH$_3$CN in 0.1% trifluoroacetic acid was used for peptide elution.

Protein or peptide samples were hydrolyzed for 20–24 hours in sealed, N$_2$-flushed, evacuated tubes in constant boiling HCl containing 4% thioglyceric acid. Amino acid analyses were performed using a fluorescamine amino acid analyzer as described in reference (6).

An ABI (Applied Biosystem, Inc.) gas-phase sequencer 470A was used for sequence analyses of carboxymethylated proteins as described in reference (7). Samples of PTH-amino acids were identified by reverse-phase HPLC on an ultrasphere ODS column as described in reference (8).

All purification steps were carried out at 4° C. Frozen cells (15 g) were suspended in three volumes (75 ml) of 7M guanidine-HCl (pH 7). The mixture was stirred for 1 h and then centrifuged for 1 h at 30,000×g. The supernatant was diluted 10-fold with Dulbecco's phosphate buffered saline (PBS) or 0.15M sodium borate buffer (pH 9.5) and then centrifuged for 30 min. at 30,000×g. Alternatively, frozen cells (25 g) were suspended in 1.5 volumes (37.5 ml) of 0.15M sodium borate buffer (pH 9.5) and stirred for 1 h. The mixture was sonicated 5 times for 30 seconds and then centrifuged for 1 h at 30,000×g. The supernatants from either guanidine-HCl extraction or sonication were mixed for 1 h on a rotating shaker with 25 ml silica (NuGel-952AC, Separation Industries, Metuchen, N.J.), and prewashed with phosphate buffered saline. The mixture was poured onto a column and the column was washed with 20-30 column volumes of 1M NaCl. The column was then eluted with 0.5M tetramethylammonium chloride in 0.01M sodium borate buffer (pH 8.0). Interferon activity was eluted in about 200 ml and separated into 4 pools. Each pool was loaded onto a monoclonal antibody (M1 2-11.1) affinity column (4 ml bed volume) equilibrated with phosphate buffered saline. After washing with 10 column volumes of phosphate buffered saline buffer, the column was eluted with either 1M guanidine-HCl or 50% ethylene glycol containing 1M NaCl and 20 mM sodium phosphate buffer (pH 7.0). Interferon activity was eluted in the first 20 ml.

Sodium dodecyl sulfate-polyacrylamide gel electrophoresis was performed as described by Laemmli (reference 9). Protein was determined by fluorescamine analysis with crystalline bovine serum albumin as the reference standard. Interferon activity was determined by a cytopathic effect inhibition assay with vesicular stomatitis virus and human WISH cells as reported in reference 10. All interferon titers are expressed in reference units/ml calibrated against the reference standard of partially purified human immune interferon.

A summary of the extraction purification procedure is presented in Table 6. The overall recovery was 25-32% and the purification was about 100 to 769 fold with an average specific activity of $1 \times 10^7$ units/mg. Total yield of rIFN-γ was 3-4 times higher with guanidine extraction (Table 6). Sodium dodecyl sulfate-polyacrylamide gel electrophresis of the last stage of purification is shown in FIG. 1. The material purified from guanidine extraction showed a single band at about 18,000 daltons (18K rIFN-γ) whereas the sonication procedure yielded a major band at about 15,000 daltons (15K rIFN-γ) and a minor band at about 17,000 daltons (FIG. 1A). On non-reducing gel, dimers and oligomers of rIFN-γ were formed (FIG. 1B).

The 18K rIFN-γ were homogeneous and the amino acid composition was consistent with the predicted from the DNA sequence (see Table 7). Amino acid composition of the 15K and 18K rIFN-65 are given in Table 7. Several hundred picomoles of reduced and carboxymethylated 15K and 18K protein underwent Edman degradation in an automatic gas-phase protein/peptide sequencer. The amino acid N-terminal sequences of first 32 residues and 25 residues of the 15K and 18K proteins were in accord with that predicted by the DNA sequence (FIG. 2). $^{14}$C-Carboxymethylated cysteines were detected in the first and third cycles of sequence analyses. No N-terminal methionine was detected. N-terminal sequence analysis of the 18K and 15K rIFN-γ demonstrated that the sequence of the area of both proteins is identical to that predicted from the DNA sequence. The C-terminal peptides have also been characterized to determine whether any deletions or changes are present in this region. Amino acid analysis carboxypeptidase A (CPA) digestion mixture indicated that serine and/or glutamine (C-terminal amino acids) were released from the 18K rIFN-γ, whereas the 15K rIFN-γ was not digested by CPA under the same condition. Since Ser-Gln was the C-terminal sequence of rIFN-γ the 18K species appeared to have the intact C-terminal residues predicted from the DNA sequence and the 15K species may have a different C-terminal residue (Lys or Arg) which is not cleaved by CPA.

The C-terminal residues predicted from the DNA sequences were further confirmed by analyzing and sequencing the C-terminal peptides after CNBr treatment. C-terminal peptides were separated on the HPLC C-18 reverse-phase column (FIG. 3). A sharp peptide peak (peak II), eluted from the early part of the gradient, was obtained from the 15K rIFN-γ and this peptide was absent from the CNBr digestion mixture of the 18K rIFN-γ. Amino acid analysis of this peptide indicated that this peptide has no homoserine or homoserine lactone and therefore must be the C-terminal CNBr peptide of the 15K protein (Table 8). Based on amino acid analysis (Table 8), this peptide corresponded to the amino acid residues No. 121-131 (no arginine was detectable). The sequence of the 11 amino acids was confirmed by sequence analysis (FIG. 2). In the case of 18K rIFN-γ, a relatively broad peak was obtained in the early part of the elution. This peak was further separated into two peaks by a shallow gradient. The amino acid analyses indicated that the first peak is the CNBr C-terminal peptide of the 18K protein (Table 8) and the amino acid composition matches the amino acid residues No. 138-146. The sequence of the 9 amino acids was verified by sequence determination (FIG. 2).

These results indicated that the 18K species was the intact rIFN-γ molecule, whereas the 15K species was a proteolytic product. The peptide bond between amino acid residues No. 131 and No. 132 (Lys-Arg) was cleaved.

TABLE 6

| Purification Step | Purification of rIFN-γ | | | | |
|---|---|---|---|---|---|
| | Total Protein mg | Total Activity units | Specific Activity unit/mg | Purification -fold | Yield % |
| I. Guanidine extraction | | | | | |
| Supernatant | 2,806 | $2.5 \times 10^8$ | $9 \times 10^4$ | — | 00 |
| Silica | 98 | $1.0 \times 10^8$ | $1 \times 10^6$ | 11 | 40 |
| Monoclonal Antibody | 8 | $0.8 \times 10^8$ | $1 \times 10^7$ | 110 | 2 |
| II. Sonification | | | | | |

TABLE 6-continued

| | Purification of rIFN-γ | | | | |
|---|---|---|---|---|---|
| Purification Step | Total Protein mg | Total Activity units | Specific Activity unit/mg | Purification -fold | Yield % |
| Supernatant | 6,136 | $8.0 \times 10^7$ | $1.3 \times 10^4$ | — | 100 |
| Silica | 87 | $4.5 \times 10^7$ | $5.2 \times 10^6$ | 400 | 56 |
| Monoclonal Antibody | 2 | $2.0 \times 10^7$ | $1.0 \times 10^7$ | 769 | 25 |

Details of purification procedure were described under "Experimental Procedures".

TABLE 7

Amino Acid Compositions of 15K and 18K rIFN-γ

| | | 15K 1-131 %131 | 18K 1-146 %146 | 18K 1-146 %146 | 15K 1-131 %131 |
|---|---|---|---|---|---|
| Asp | D | (20) | 20.9 | (20) | 19.9 |
| Thr | T | (5) | 5.1 | (5) | 4.9 |
| Ser | S | (9) | 9.8 | (11) | 6.7 |
| Glu | E | (16) | 18.5 | (18) | 15.1 |
| Pro | P | (2) | (2)* | (2) | (2) |
| Gly | G | (4) | 5.9 | (5) | 5.6 |
| Ala | A | (7) | 8.2 | (8) | 7.3 |
| Cys | C | (2) | (2)* | (2) | (2) |
| Val | V | (8) | 9.1 | (8) | 9.1 |
| Met | M | (3) | 4.7 | (4) | 3.8 |
| Ile | I | (7) | 7.2 | (7) | 6.6 |
| Leu | L | (9) | 10.5 | (10) | 9.6 |
| Tyr | Y | (5) | 5.5 | (5) | 4.8 |
| Phe | F | (9) | 10.3 | (10) | 8.2 |
| His | H | (2) | 1.8 | (2) | 2.5 |
| Lys | K | (19) | 19.9 | (20) | 16.9 |
| Arg | R | (3) | 8.6 | (8) | 5.6 |
| W | | (1) | (1)* | (1) | (1)* |

≠Figures in parenthesis indicate the predicted residue number from DNA sequence.
*Values for Proline, cystine and tryptophan were not determined.

TABLE 8

CNBr C-terminal Peptides of 15K and 18K

| | | 15K | | 18K | |
|---|---|---|---|---|---|
| Asp | D | | | | |
| Thr | T | 0.9 | (1) ≠ | | |
| Ser | S | 1.1 | (1) | 0.84 | (1) |
| Glu | E | 1.1 | (1) | 1.1 | (1) |
| Pro | P | * | (1) | | |
| Gly | G | 1.5 | (1) | 1.3 | (1) |
| Ala | A | 2.4 | (3) | 1.1 | (1) |
| Cys | C | | | | |
| Val | V | | | | |
| Met | M | | | | |
| Ile | I | | | | |
| Leu | L | 1.0 | (1) | 1.1 | (1) |
| Tyr | Y | | | | |
| Phe | F | | | 1.0 | (1) |
| His | H | | | | |
| Lys | K | 1.9 | (2) | 2.8 | (3) |
| Arg | R | | | | |
| Positions in sequence | | 121-131 | | 138-146 | |

Figures in parenthesis indicate the predicted residue number from DNA sequence.
*Value for Proline was not determined.

REFERENCES

1. Gray, P. W. et al. (1982) Nature 295, 503-508.
2. Staehelin, T. et al. (1981) J. Biol. Chem. 256, 9750-9754.
3. Allen, G. Sequencing of Protein and Peptides, (1981) North-Holland Publishing Co., Amsterdam, New York pp. 30-31.
4. Amber, R. P. (1967) Methods in Enzymol. 11, 436-445.
5. Wolfe, R. A. and Stein, S. (1982) Modern Methods in Pharmacology pp. 55-77, Alan R. Liss, Inc. New York, N.Y.
6. Stein, S. and Brink, L. (1981) Methods in Enzymology, 79, 20-25.
7. Hewick, R. M. Hunkapillar, M. W., Hodd, L. E. and Dreyer, W. I. (1981) J. Biol. Chem. 256, 7990-7997.
8. Hawke, D., Yuan, P-M., and Shively, J. E. (1982) Anal. Biochem. 120, 302-311.
9. Laemmli, U.K. (1970) Nature 227, 680-685.
10. Rubinstein, S., Familletti, P. C., and Pestka, S. (1981) J. Virol. 37, 755-758.

What is claimed is:

1. A method for extracting intact recombinant human immune interferon from transformed microorganisms containing this protein comprising extracting said transformed microorganisms with a protease inhibitor.
2. The method of claim 1 wherein the protease inhibitor is guanidine-HCl.
3. The method of claim 1 wherein the transformed microorganisms are suspended in a solution of guanidine-HCl.
4. The method of claim 3 wherein the solution is at least about 4M guanidine-HCl.
5. The method of claim 1 wherein the intact mature recombinant human immune interferon protein has a molecular weight of about 18,000 daltons.
6. The method of claim 1 wherein the transformed microorganisms preparation is separated after being treated with the protease inhibitor into a supernate fraction and cell debris fraction.
7. The method of claim 6, wherein the protease inhibitor is guanidine-HCl.